United States Patent [19]

Drewlow

[11] Patent Number: Plant 7,291

[45] Date of Patent: Aug. 7, 1990

[54] KALANCHOE PLANT NAMED LEMON DROP

[75] Inventor: Lyndon W. Drewlow, Ashtabula, Ohio

[73] Assignee: Mikkelsens, Inc., Ashtabula, Ohio

[21] Appl. No.: 318,058

[22] Filed: Mar. 2, 1989

[51] Int. Cl.[5] ..... A01H 5/00

[52] U.S. Cl. ..... Plt./68

[58] Field of Search ..... Plt./68

[56] References Cited

U.S. PATENT DOCUMENTS

P. 3,389 8/1973 Irwin ..... Plt. 68
P. 3,854 3/1976 Grob ..... Plt. 68
P. 4,726 5/1981 Mikkelsen et al. ..... Plt. 68
P. 6,340 10/1988 Van der Knaap ..... Plt. 68
P. 6,391 11/1988 Hesse ..... Plt. 68

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Kalanchoe plant named Lemon Drop particularly characterized by its tall, upright stems which provide the ability to produce cut flowers. Lemon Drop has light yellow flowers, relatively large leaves, excellent lateral branching, open inflorescence, and long lasting flowers which retain color with aging and which remain open under low light conditions.

1 Drawing Sheet

The present invention relates to a new and distinctive cultivar of Kalanchoe plant, botanically known as *Kalanchoe blossfeldiana,* and known by the cultivar name Lemon Drop. The new cultivar was developed by me through controlled breeding by crossing Mikkelsen Seedling No. 83-2249-2 (seed parent) with Yellow Sun (pollen parent). A principal objective of the breeding program was to develop new Kalanchoe cultivars having certain desired characteristics and which could be used to produce cut flowers.

Asexual reproduction of stem cuttings has shown that the unique features of this new Kalanchoe are stabilized and are reproduced true to type in successive propagations.

The following characteristics distinguish the new Kalanchoe from both its parent cultivars and other cultivated Kalanchoe of this type known and used in the floriculture industry. In order to describe the characteristics more meaningfully, references are made to known pot type Kalanchoe cultivars, including Fortyniner (U.S. Plant Pat. No. 5,256) and Goldstrike (U.S. Plant Pat. No. 6,632). Also referred to are Desert Blaze, Sombrero, Passionate and Bashful, all cut flower type cultivars of applicant disclosed in pending plant patent applications.

1. Lemon Drop is an upright, tall cut flower type Kalanchoe characterized by light yellow flowers which are lighter in color than the bright yellow Fortyniner and the golden yellow Goldstrike, both pot type Kalanchoe.

2. Lemon Drop is much taller (53–57 cm) than the two pot type Kalanchoes noted above (both 22–26 cm), and is slightly taller than Sombrero (43–47 cm), Desert Blaze (48–52 cm), Bashful (48–52 cm), and Passionate (43–47 cm).

3. Lemon Drop generally has eight lateral branches similar to Goldstrike, Fortyniner and Desert Blaze, while Passionate, Bashful and Sombrero usually have ten lateral branches.

4. Lemon Drop is approximately one week earlier to flower than Fortyniner and Goldstrike, but similar to the other four cut flower type Kalanchoes.

5. Flower size of Lemon Drop is larger (16 mm) than Passionate, Goldstrike and Fortyniner, similar to Desert Blaze and Sombrero, but not as large as Bashful (22 mm).

6. Leaves of Lemon Drop are smaller than Sombrero, but larger than all the rest of the comparison cultivars.

7. Mature stigmatic surfaces of Lemon Drop remain hidden below the anthers while all the rest of the cultivars show the whitish mature stigmatic surface between and slightly below the upper four anthers.

8. Leaf margins have large lobes and shallow serration, while all other comparisons are more deeply serrated and finer lobed.

9. The five cut flower type Kalanchoes tend to have very little basal branching from the lower two nodes, while the two pot Kalanchoe cultivars noted tend to branch at all nodes except the bottom node next to the soil line.

10. The inflorescence of Lemon Drop and the other four cut flower types are open with flowers carried at the ends of long branches, while the pot types have dense compact inflorescence with flowers on the end of short branches.

11. Long lasting flowers that do not fade easily as the flower ages.

12. Strong, upright stems.

13. Flowers remain open under low light conditions after one dark to light conditioning cycle after cutting.

14. Can be grown on a schedule to provide cut flowers every week of the year.

The accompanying colored photograph is a top perspective view, illustrating the overall appearance of Lemon Drop. The photograph shows the color as true as it is reasonably possible to obtain in a colored reproduction of this type. The photograph was taken in late June 1988.

The following is a detailed description of my new Kalanchoe cultivar based on plants produced under commercial practices in Ashtabula, Ohio, under greenhouse conditions. Color references are made to The Royal Horticultural Society Colour Chart except where general color terms of ordinary dictionary significance are used.

The description is based on plant cuttings five (5) weeks old stuck in six (6) inch pots and given two (2) weeks of long days and than short days to induce flowering. The plants were grown at 64°–68° F. night temperatures. Measurements were taken twelve (12) weeks after the start of short days, with plant height being measured from the soil line of the plant.

Parentage: A controlled cross between female parent Mikkelsen Seedling 83-2249-2 and male parent Yellow Sun.

Propagation:

(A) *Type cutting.*—Stem tip cutting up to 3 cm long.

(B) *Time to root.*—10 days at 21° C. summer; 14 days at 21° C. winter.

(C) *Rooting habit.*—Abundant, fine, fibrous.

Plant description:

(A) *Form.*—Tall (53–57 cm), upright, flower clusters (inflorescence) are carried above the main leaf mass on long strong stems; larger leaves appear near the basal portion of plant with smaller leaves in the flower cluster.

(B) *Habit of growth.*—Upright, branching occurs from several nodes in the middle of the plant producing a spray form of flower cluster; an occasional branch from the lower two noses. Environment will play a role in final height of plant.

(C) *Foliage.*—Leaves simple and opposite. (1) Size: Average full grown leaf on a plant grown in a 15 cm pot is 140 to 150 mm long and 90 to 95 mm wide; leaves in flower cluster smaller; growth conditions will cause leaf size to vary. (2) Shape: Ovate; apex obtuse; base is rounded. (3) Texture: Glabrous, coriaceous and succulent. (4) Margin: Upper half of leaf slightly crenate and lower half crenate. (5) Color: Young foliage, top size near 146B; Young foliage, under side near 146C; Mature foliage, top side near 147A; Mature foilage, under side between 147A and 147B.

Flowering description:

(A) *Flowering habits.*—Inflorescence is a cyme. Terminal flower on main axis opens first followed by the terminal flowers of the side branches, continuing with the subsequent development of branches in the inforescence. Inflorescence is made up of the main stem and up to eight lateral branches. The inforescence is 40–43 cm in height and 18–20 cm in diameter, and is open.

(B) *Natural flowering season.*—Early January. Flowering time under controlled daylength at 20° C. in summer is nine weeks; in winter is twelve weeks. Flowering time depends on temperature, light intensity and other growing conditions. In general, higher temperatures (to the point of heat delay) and increased light intensity will speed up flowering, and low temperatures and light intensity will delay flowering. Other conditions that can cause delay in the flowering are low fertility, very high night temperature (80° F. plus) and moisture stress.

(C) *Flower buds.*—Oblong, up to 9 mm long just before showing first color, developing tubular as flower petals mature; sheathed with four green sepals.

(D) *Flowers borne.*—Compound dichasial cymes, primary peduncle 8 mm in diameter just below the first branch of the inforescence. Length will vary with growing conditions. In general, peduncles will be shorter when plants are moisture stressed, grown well spaced, grown under high light intensity, grown under low temperatures, or are given applications of growth regulators. If plants are grown crowded and/or under low light conditions, the peduncles will tend to stretch badly. Pedicels will vary in length depending on where they are located. The pedicels become shorter the higher they are in the inflorescence, that is, the closer they are to the apical meristem.

(E) *Quantity of flowers.*—Highly floriferous as central axis can have up to 150 or more flowers and laterals up to 75 flowers. Flower clusters are more or less indeterminant in nature.

(F) *Petals.*—(1) Shape: Nearly rounded, top cuspidate. (2) Color: Top side when opening 20A, fading to 20B; under side 20C. (3) Number of Petals: 4. (4) Size: 8 mm long, 7 mm wide; total flower diameter 16 mm.

(G) *Reproductive organs.*—(1) Number of Stamens: Eight. (a) Anther shape: Flat elliptical; color — yellow. (b) Filament color: Light green. (c) Pollen color: Yellow. (2) Pistils: (a) Stigma shape: Flat; color — greenish-yellow. (b) Style color: Greenish yellow. (c) Ovaries: Number — 4; size — 5 mm; color — green.

Disease resistance: Lemon Drop has shown good resistance to powdery mildew.

I claim:

1. A new and distinct cultivar of Kalanchoe plant named Lemon Drop, as illustrated and described.

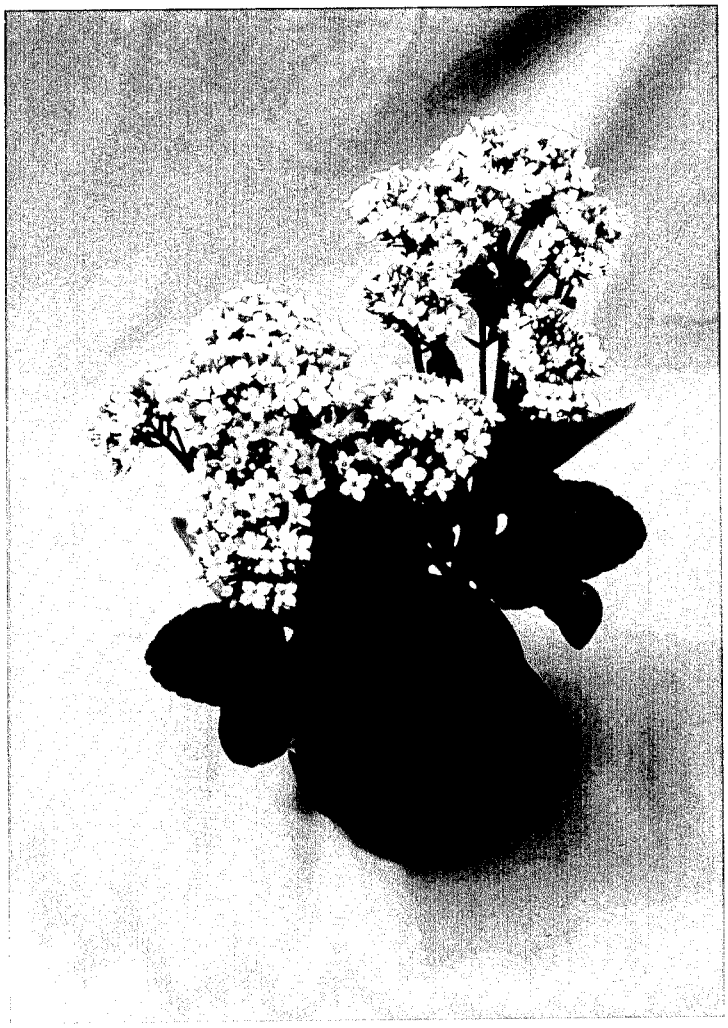

* * * * *